(12) United States Patent  (10) Patent No.: US 7,886,908 B2
Farrar et al.  (45) Date of Patent: Feb. 15, 2011

(54) TRAY ASSEMBLY

(75) Inventors: Quinton Farrar, Keene, NH (US); Mary Beth Padgett, Greensboro, NC (US); Jason Dillon, Alstead, NH (US)

(73) Assignee: Smiths Medical ASD, Inc., Keene, NH (US)

( * ) Notice: Subject to any disclaimer, the term of this patent is extended or adjusted under 35 U.S.C. 154(b) by 0 days.

(21) Appl. No.: 12/458,625

(22) Filed: Jul. 17, 2009

(65) Prior Publication Data

US 2010/0012537 A1  Jan. 21, 2010

Related U.S. Application Data

(60) Provisional application No. 61/129,815, filed on Jul. 21, 2008.

(51) Int. Cl.
  *B65D 83/02* (2006.01)
(52) U.S. Cl. .................. 206/370; 206/366; 206/564; 206/459.5; 206/364
(58) Field of Classification Search .......... 206/364, 206/363, 370, 366, 438, 564, 565, 477, 480, 206/459.5, 570; 604/198, 192, 263; 53/475, 53/473, 467
See application file for complete search history.

(56) References Cited

U.S. PATENT DOCUMENTS

| | | | | |
|---|---|---|---|---|
| 4,243,140 A | * | 1/1981 | Thrun | 206/380 |
| 4,349,338 A | * | 9/1982 | Heppler | 434/262 |
| 4,383,615 A | | 5/1983 | Aquino | |
| 4,501,363 A | | 2/1985 | Isbey, Jr. | |
| 4,595,102 A | * | 6/1986 | Cianci et al. | 206/572 |
| 4,736,850 A | * | 4/1988 | Bowman et al. | 206/570 |
| 4,974,728 A | * | 12/1990 | Colton | 206/366 |
| 5,522,503 A | * | 6/1996 | Halbich | 206/366 |
| 5,647,849 A | | 7/1997 | Kalin | |
| 5,665,075 A | | 9/1997 | Gyure et al. | |
| 5,779,053 A | * | 7/1998 | Partika et al. | 206/570 |
| 5,823,363 A | * | 10/1998 | Cassel | 211/60.1 |
| 5,941,394 A | * | 8/1999 | Siegler | 206/571 |
| D489,454 S | * | 5/2004 | Koseki | D24/131 |
| 6,769,546 B2 | | 8/2004 | Busch | |
| 6,814,236 B2 | * | 11/2004 | Roshdy | 206/570 |
| 7,048,120 B2 | * | 5/2006 | Pond | 206/366 |

(Continued)

*Primary Examiner*—David T Fidei
(74) *Attorney, Agent, or Firm*—Louis Woo

(57) ABSTRACT

An allergy testing tray assembly has an outer tray and an inner tray fitted in the outer tray. Each one piece tray is molded to have three longitudinal areas separated by two rows of spaced posts. A plurality of allergy testing needles are removably held between the adjacent posts. These syringes each have needle protective housing and a sheath that covers the needle prior to use color coded to reflect the gauge of the needle of the syringe. The plunger end of each of the syringes is capped so that each syringe is isolated from the environment. The trays are sealed by a cover sheet that may also have markings in the same color as the color of the housing and the sheath, so that a clinician can readily tell the gauge of the needle of the syringes stored in the trays, without having to remove the cover sheet. Once the tray assembly is sterilized, the sterility of the syringe are doubly protected by the sealing of the needle end and the plunger end of the syringe as well as the sealing of the trays from the environment by the cover sheet.

20 Claims, 10 Drawing Sheets

U.S. PATENT DOCUMENTS

| | | |
|---|---|---|
| 7,250,038 B2 | 7/2007 | Simpson et al. |
| 2002/0185406 A1* | 12/2002 | Massengale et al. ........ 206/571 |
| 2005/0119622 A1* | 6/2005 | Temple ....................... 604/189 |
| 2006/0264822 A1* | 11/2006 | Nagamatsu .............. 604/97.02 |
| 2006/0283745 A1* | 12/2006 | Massengale et al. ........ 206/438 |
| 2007/0142786 A1* | 6/2007 | Lampropoulos et al. .... 604/189 |
| 2007/0208311 A1* | 9/2007 | Farrar et al. ................. 604/187 |
| 2009/0026108 A1* | 1/2009 | Ross .......................... 206/570 |

* cited by examiner

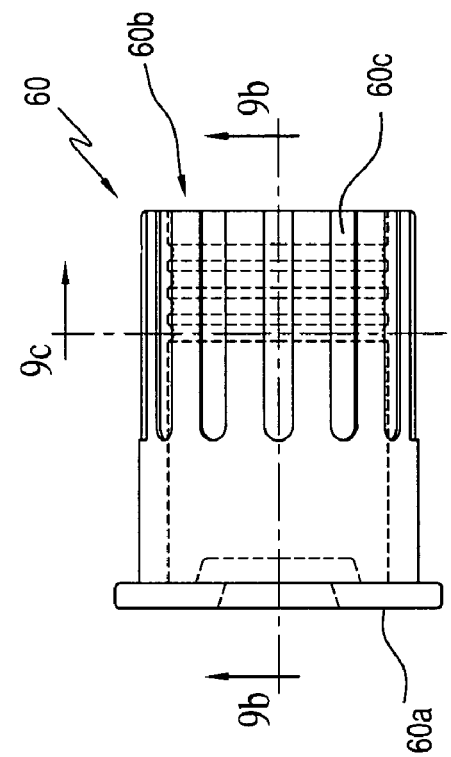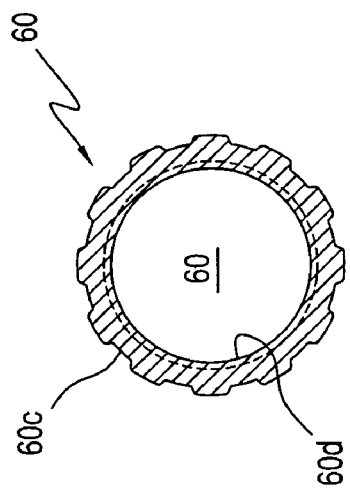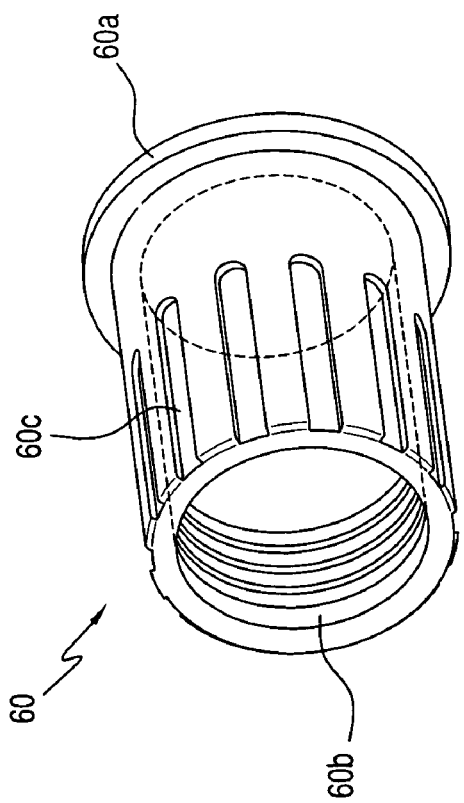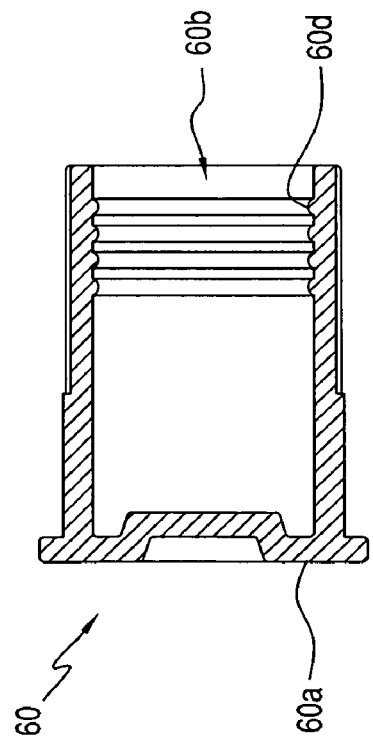
FIG. 9a
FIG. 9c
FIG. 8
FIG. 9b

TRAY ASSEMBLY

FIELD OF THE INVENTION

The present invention relates to trays for holding multiple syringes, and particularly relates to a tray assembly that has multiple trays each containing a plurality of syringes that may be used for testing allergies in a patient.

BACKGROUND OF THE INVENTION

Allergy tray syringes are typically used in a clinic setting to inject several different allergens under the skin of a patient to determine if the patient has allergic reactions to the allergens. These allergens are usually in the form of allergy reactant serums that the clinician pre-fills the syringes with. Often, all of the syringes in the allergy tray package are not used for one set of tests on one patient, and clinics will either keep these syringes on the shelf and use them for testing at another time or discard them.

The currently being sold allergy trays are stocked with syringes that remain sterile only if the allergy trays are sealed. Once the seals are removed, the syringes stored in these allergy trays are exposed to the environment and are no longer sterile.

Some time ago, to promote its allergy syringes, the Becton Dickinson company offered a free syringe needle organizer tray to purchasers of its allergy syringes. This give away tray has two layers for storing the allergy syringes. When shipped out to purchasers of allergy syringes, these trays were not sealed. The syringes used with the give away tray in turn are not sealed from the environment. Thus, once removed from their packages, the syringes to be used with the give away allergy tray are no longer sterile.

SUMMARY OF THE PRESENT INVENTION

The present invention tray assembly provides sterility protection of the allergy syringes stored in layered trays. The tray assembly has an inner tray and an outer tray, which may also be referred to as an insert tray and a base tray. Each of the trays is molded from a plastic material such as styrene, and is formed to provide a plurality of slots to which the syringes are held. The slots are numbered consecutively, preferably starting with the lowest number at one end of the insert tray and continuing to the base tray. A plurality of slots, for example 13 and 12, may be provided on the insert tray and base tray, respectively, so that a total of 25 slots are available for removably holding 25 syringes in the inventive tray assembly. The syringes stored in each of the insert and base trays of the tray assembly may be allergy testing syringes. The numbering on the trays provides an easy correlation with the test serums pre-filled in the various syringes for testing so that ready identification can be made on which of the test serums causes an allergic reaction in a patient.

The base tray has an indented inner peripheral shoulder. The insert tray has an outer peripheral lip that rests on the inner peripheral indented shoulder of the base tray, when the insert tray is fitted into the base tray, with the respective top surfaces of the insert and base trays lying along the same plane. A cover sheet is removably bonded to at least the top peripheral surface of the base tray, so as to isolate the inside of the trays from the environment and to therefore maintain sterility inside the tray once the tray has undergone a sterilization process.

Each of the syringes has a plunger end and a needle end to which a fixed needle is permanently attached. Although a fixed needle syringe is being disclosed, it should be appreciated that a syringe that has a luer end to which a needle assembly is coupled may also be used. A sheath connects to the needle end for covering the needle that extends from the syringe, or from the luer in the case of a lured syringe. Also attached to the needle end is a needle protective housing that is pivotable to cover the needle, after the sheath has been removed from the needle. Both the sheath that covers the needle prior to use and the needle protective housing that covers the needle, after the sheath is removed and the needle presumably used and therefore contaminated, are molded to have a color that corresponds to the gauge of the needle, and may be in accord with accepted international standards for medical devices, so that a clinician only has to look at the color of either the sheath, the protective housing or both to determine the gauge of the needle for that syringe.

The allergy syringes stored in the trays each have a syringe body that has extending from its finger flange an annular extension, or well, dimensioned to allow the plunger end of the syringe to be sealingly capped. Thus, with the sheath sealingly covering the needle and a cap sealing covering the plunger end, the syringe of the instant invention is a self-contained syringe with a sterile fluid path.

The tray assembly of the present invention accordingly is a sealed tray that has stored therein a plurality of self contained allergy testing syringes that are color coded to the gauge of the needle of the syringes.

In practice, the plurality of syringes stored in the insert and base trays all have needles that are the same gauge so that all of the syringes have sheaths and needle protective housings that are the same color. So that a user can determine the gauge of the needles of the syringes stored inside the tray assembly, the information or markings on the cover sheet are printed in the same color as that of the needle protective housing and sheath of the syringes stored in the trays. Alternatively, the cover sheet itself may have the same color coded to reflect the gauge of the needles of the syringes stored in the tray while the information or markings on the cover sheet may be a different color for ease of reading.

The present invention therefore is directed to a tray assembly that comprises a one piece molded base tray and a one piece molded insert tray each having a plurality of slots each adapted to removably hold a syringe. The base tray has a top with an indented inner periphery configured to hold an outer peripheral lip of the inner tray so that the respective top peripheral surfaces of the insert and base trays lie along the same plane when the insert tray is fittingly placed into the base tray. A plurality of syringes are correspondingly fitted to the slots. The slots are numbered for assigning a particular number to each of the syringes, each of which has a needle end wherefrom a needle extends and a lunger end wherethrough a plunger is movable. A sheath sealingly covers the needle end and a cap sealingly covers the plunger end of each of the syringes so that each syringe remains sterile prior to use. A cover sheet sealingly and removably bonds to at least the top peripheral surface of the base tray to maintain the sterility inside the insert and base trays, and to shield the syringes stored in the trays from the environment.

The present invention is also directed to a combination that includes a one piece molded base tray and a one piece molded insert tray each having a plurality of slots each adapted to removably hold a syringe. The slots are consecutively numbered starting from one of the trays and continuing to the other of the trays. The base tray has a top with an indented inner periphery configured to hold an outer peripheral lip of the insert tray so that the respective top peripheral surfaces of the insert and base trays lie co-planarly when the insert tray is fittingly placed in the base tray. The combination further includes a plurality of syringes each fitted to a corresponding one of the slots in the trays such that a particular number is assigned to each of the syringes. The syringes each have a needle wherefrom a needle extends and whereto a needle protective housing is attached, and a plunger end wherethrough a plunger is movable. A sheath sealingly covers the needle end and a cap sealingly covers the plunger end of each of the syringes so that each syringe remains sterile prior to use. A cover sheet sealingly and removably bonded to at least the top peripheral surface of the base tray to maintain sterility inside the trays and to shield the syringes stored in the tray from the environment.

The present invention further relates to a method of providing a plurality of syringes for use by a patient that comprises the steps of: molding a one piece base tray having a top with an indented inner periphery and a plurality of slots each adapted to removably hold a syringe, molding a one piece insert tray having an outer peripheral lip adapted to rest on the indented inner periphery of the base tray so that respective top peripheral surfaces of the insert and base trays lie co-planarly when the insert tray is placed in to the base tray, the insert tray having a plurality of slots each adapted to removably hold a syringe, and the slots in the insert and base trays are consecutively numbered starting from one of the trays and continuing to the other of the trays. The method of the instant invention further includes the step of storing a plurality of syringes each to a corresponding one of the slots in the insert and base trays such that a particular number is assigned to each of the syringes, each of the syringes having a needle end wherefrom a needle extends and whereto a needle protective housing is attached and a plunger end wherethrough a plunger is movable, a sheath sealingly covering the needle end and a cap sealingly covering the plunger end of each of the syringes so that each syringe remains sterile prior to use. The method furthermore includes the step of placing the insert tray into the base tray, and the step of sealingly bonding a removable cover sheet to at least the top peripheral surface of the base tray to shield the syringes stored in the trays from the environment.

Another aspect of the invention includes the color coding of the syringes and the cover sheet to the gauge of the needle of the syringes, so that a clinician can look at the color of the information printed on the cover sheet, or the color of the cover sheet itself, to determine the gauge of the needle of the syringes stored in the trays, and thereafter can continually determine the gauge of the needle of each of the syringe by referencing the color of the needle protective housing and sheath of syringe.

Yet another aspect of the invention is the covering of both the needle end and the plunger end of each of the syringe by respective sheath and cap, so that each of the syringes in the tray assembly is doubly protected from the environment, and therefore remains sterile collectively in the trays, and individually after the cover sheet has been removed from the trays.

BRIEF DESCRIPTION OF THE FIGURES

The present invention will become apparent and the invention itself will be best understood by reference to the following description of the invention taken in conjunction with the following drawings, wherein:

FIG. 6 is a perspective view of the needle sheath of the syringe shown in FIG. 5a;
FIG. 8 is a perspective view of the cap for covering the plunger end of the FIG. 5a syringe;
FIG. 9a is a side view of the FIG. 8 cap;
FIG. 9b is a cross-sectional view along section E-E of the FIG. 9a cap;
FIG. 9c is a cross-sectional view along section D-D of the FIG. 9a cap.

DETAILED DESCRIPTION OF THE INVENTION

Figure 1:
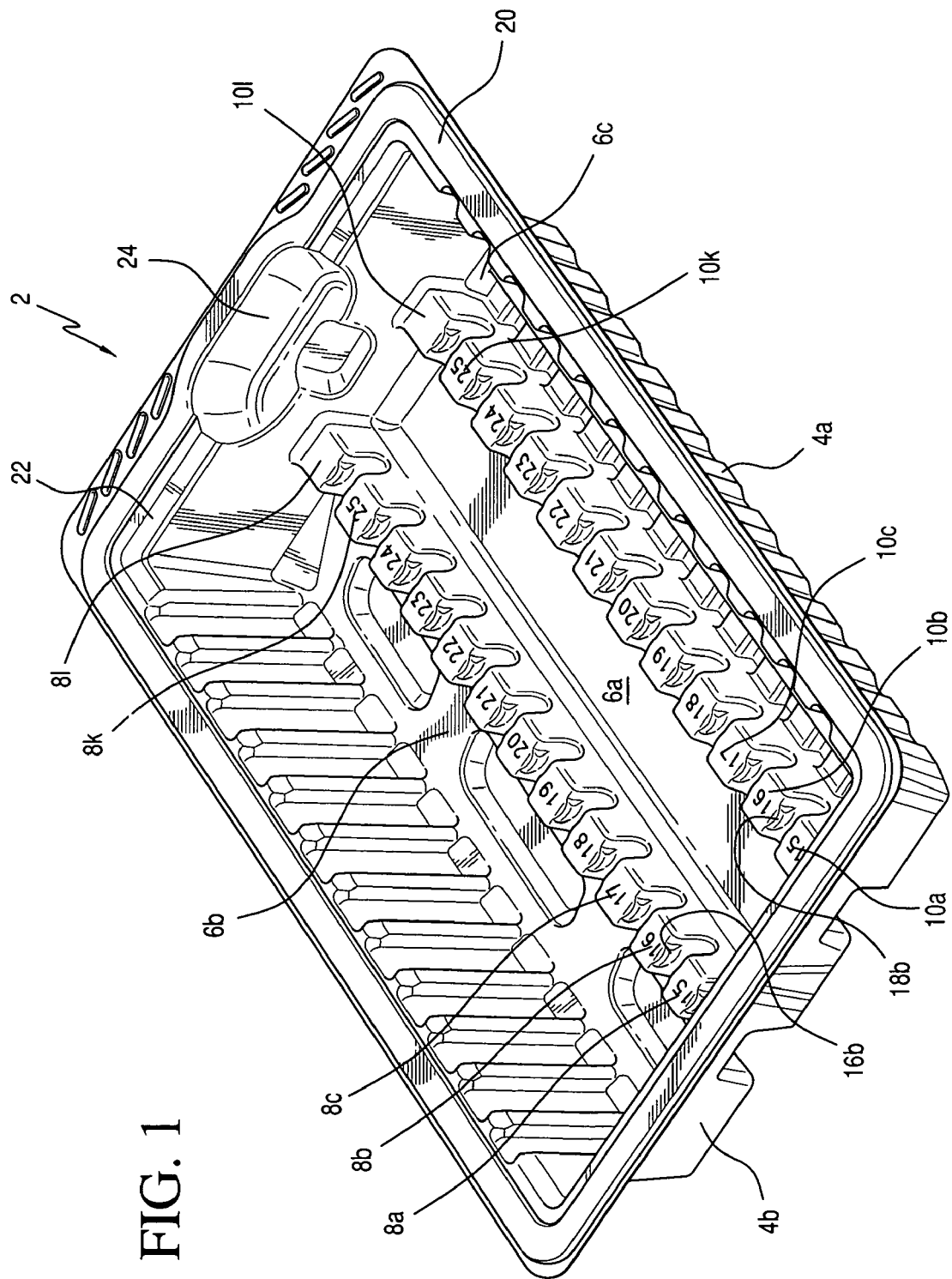
FIG. 1 is a perspective view of the outer or base tray of the present invention.
Figures 2A, 2B:
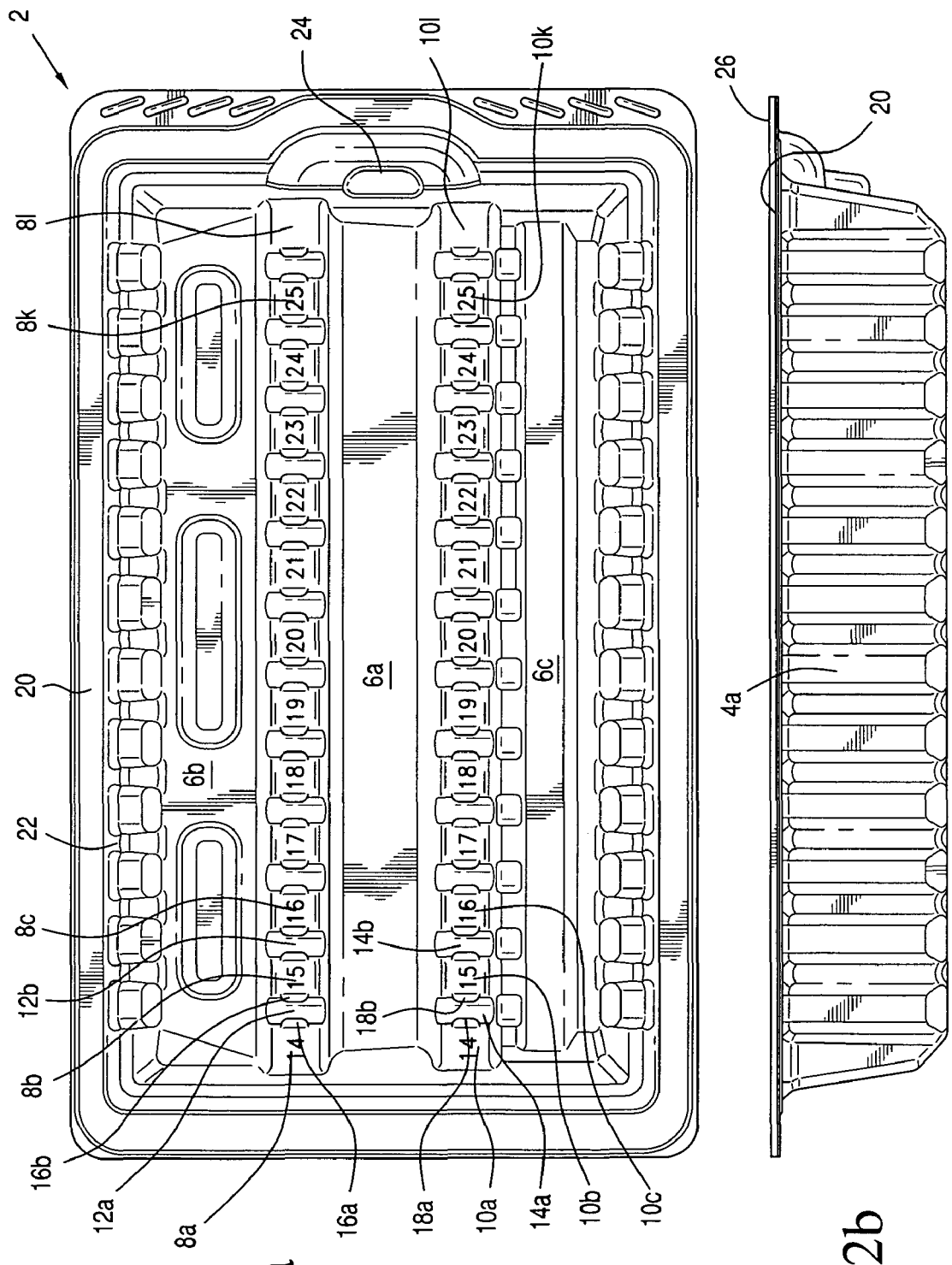
FIG. 2a is a plan view of the FIG. 1 base tray.
FIG. 2b is a side view of the FIG. 1 base tray.
Figure 2C:
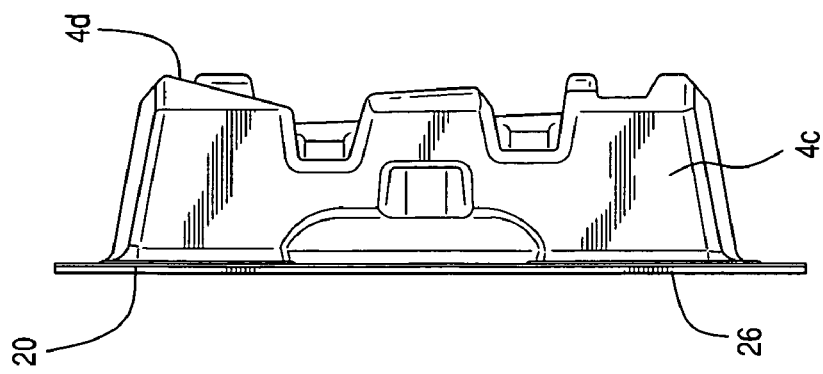
FIG. 2c is a side end view of the FIG. 1 base tray.
Figure 2D:
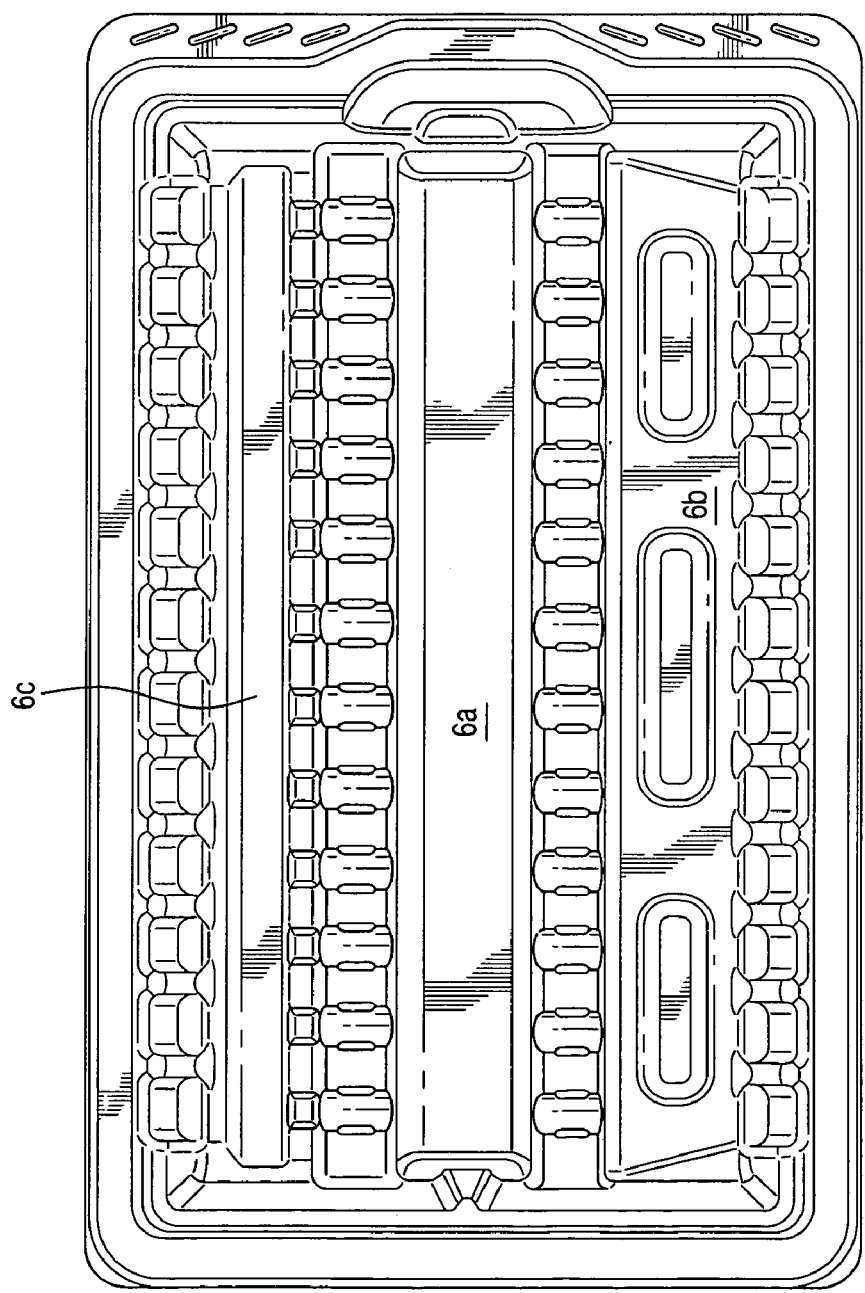
FIG. 2d is a bottom view of the FIG. 1 base tray.

With reference to FIGS. 1 and 2a to 2d, an outer or base tray 2 is shown to have four sidewalls 4a, 4b, 4c and 4d (not shown). The base tray is a one piece unitary tray molded from a conventional medical plastics material such as for example styrene, so that particular formations may be made when the tray is molded. In particular, the tray is moldingly configured to have three longitudinal areas 6a, 6b and 6c, best shown in FIG. 2a. Per shown in FIGS. 1 and 2a, these longitudinal areas, also seen from the bottom view of FIG. 2d, are separated by two longitudinal rows of aligned posts 8 and 10 of which 8a, 8b, 8c and 8l are designated for row 8 and 10a, 10b, 10c and 10l are designed for row 10. Adjacent posts such as for example posts 8a and 8b are separated by a space 12a that is dimensioned to accept the body of a syringe, such as that shown in FIG. 5a. The same dimensioned space, such as 12b, separates adjacent posts, for example 8b and 8c, all along the row of post to post 8l. The same is true with respect to the row of posts 10a-10l, as each adjacent pair of posts is separated by a space, for example post 10a and 10b being separated by space 14a and post 10b and 10c separated by space 14c, etc.

At the opposed surfaces of adjacent posts along each row of posts are ridges or protuberances, for example ridges 16a and 16b at the opposed surfaces of posts 8a and 8b, respectively, and ridges 18a and 18b between posts 10a and 10b, respectively. Thus configured, respective aligned spaces such as for example 12a, 14a and 12b, 14b for rows 12 and 14, respectively, are formed in alignment in tray 2. These in alignment spaces form the slots into which the body of the syringe such as that shown in FIG. 5a may be press fittingly stored. Once fitted into a slot, the syringe is held in place by the ridges 16 and 18 at the opposed surfaces of the adjacent posts that form the slot, as the ridges, being plastic, tend to return to their original shapes after the syringe body is press fitted into the space past the ridges. An exemplar 12 slots are shown to be formed by the in alignment spaces defined by the two rows of posts 8 and 10 in the base tray 2 shown in FIGS. 1 and 2.

Figure 3:
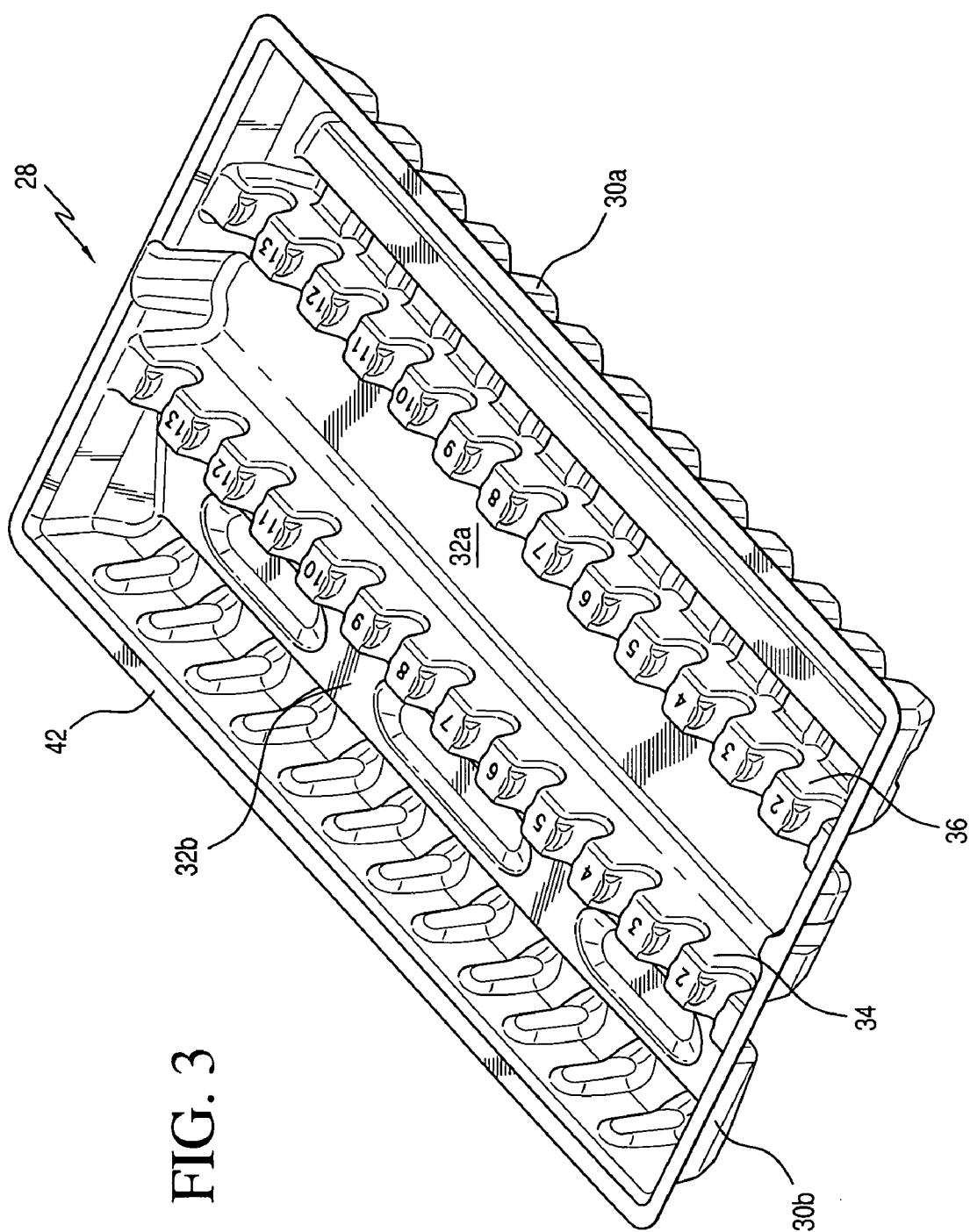
FIG. 3 is a perspective view of the inner or insert tray of the present invention.

As further shown in FIGS. 1 and 2b, base tray 2 has a top surface 20 along its periphery, and an indented shoulder 22 along its periphery. A concave space 24 is provided at one end of tray 2. As best shown in FIGS. 2b and 2c, a cover sheet 26 is attached to the top surface 20 of base tray 2 for sealingly isolating the interior of base tray 2 (and also the insert tray shown in FIG. 3 after it has been fittingly positioned into tray 2), and the syringes that are stored in the trays. Cover sheet 26 may be made from an air impermeable material such as paper, thin plastic, cellophane, etc. For the instant embodiment, cover sheet 26 is made from Tyvek. After sterilization, the interior of tray 2, the insert tray therein and the syringes stored in those trays remain isolated from the environment and therefore stay sterile until cover sheet 26 is peelingly removed from tray 2. It should be appreciated that the cover sheet 26 shown in FIGS. 2b and 2c is in fact not drawn to scale, as the cover sheet in actuality is relatively thin and the cover sheet 26 in those figures was drawn for illustration and explanation purposes only.

Although not shown, cover sheet 26 may have a color coded to the gauge of the needle of the syringes stored in the trays, as will be discussed later. Alternatively, instead of the cover sheet 26 being color coded, only the markings or information printed on the cover sheet may be effected in a color that signifies the gauge of the needle of the syringes stored in the trays. For the sake of illustration, cover sheet 26 is not shown to cover tray 2 in the perspective view of FIG. 1 or the plan view of FIG. 2b. It should be noted that even though the base tray 2 thus disclosed is molded from white virgin styrene, a color that represents or corresponds to the gauge of the needle stored in the base tray may be added to the molding material, so that base tray 2 may be molded to be a one piece tray that is color coded to the gauge of the needle of the syringes stored in the tray. For the embodiment disclosed, assume the needle for the allergy testing syringe is a 27 gauge needle and the color that represents the 27 gauge needle is gray. Thus, in addition to the markings on cover sheet 26 that are printed gray, base tray 2 may also be molded from a gray plastics material, for example gray colored styrene.

Figure 4A:
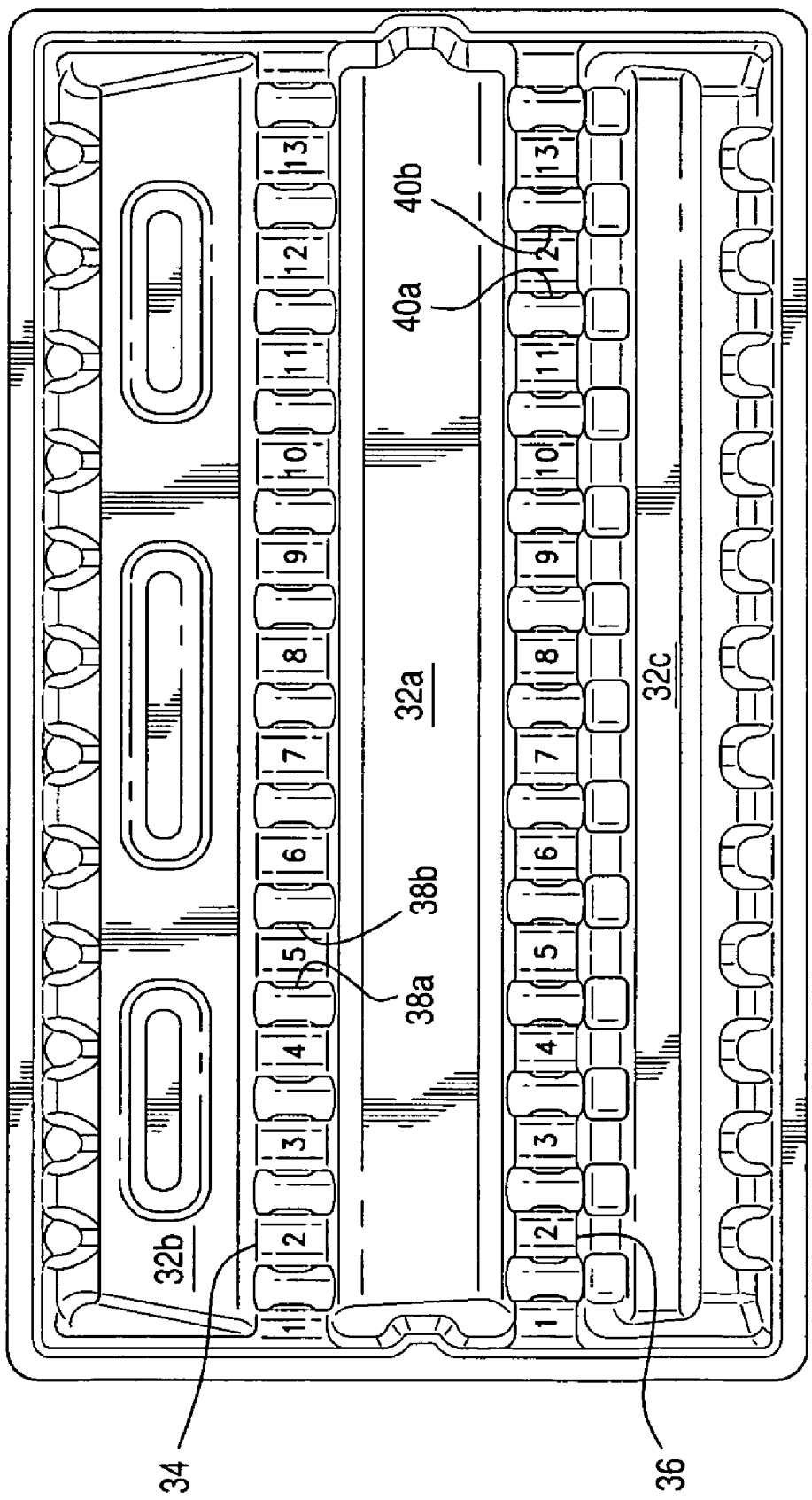
FIG. 4a is a plan view of the insert tray of FIG. 3.
Figure 4C:
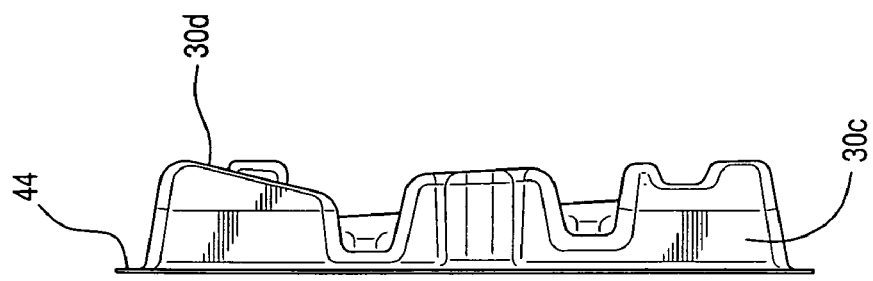
FIG. 4c is a side end view of the FIG. 3 insert tray.
Figure 4B:
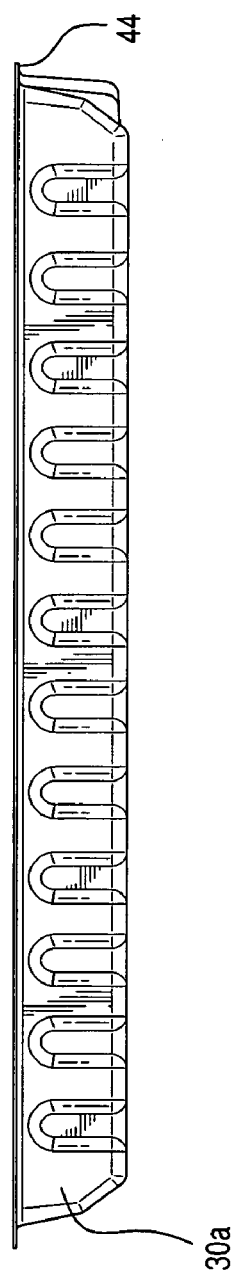
FIG. 4b is a side view of the FIG. 3 insert tray.

With reference to FIG. 3 and FIGS. 4a-4c, an inner or insert tray 28 is shown. Insert tray 28 is also a one piece molded styrene tray configured substantially the same as base tray 2. Since insert tray 28 is positioned over and fitted into base tray 2, it is a thinner tray in that its sidewalls 30a-30d (30d is not shown) have a shorter height than sidewalls 4a-4d of base tray 2. Insert tray 28 also has three longitudinal areas 32a, 32b and 32c, with area 32a separated by two rows of aligned posts 34 and 36. As shown in FIG. 4a, the posts for the respective rows 34 and 36 are numbered 1-13 to designate the 13 slots for syringes. Although numbers are not shown in the base tray 2 of FIG. 2a, it should be appreciated that the respective rows of posts 8 and 10 are numbered consecutively, starting with the number 14 and ending with the number 25, for the base tray 2 shown. The opposed surfaces of adjacent posts for each row of aligned posts 34 and 36 also have protuberances or ridges, such as 38a and 38b between adjacent posts numbered 3 and 4 in rows 34 and ridges 40a and 40b between posts numbered 12 and 13 for row 36. Thus, the body of the syringe may be press fitted into the respective spaces between adjacent posts that are in alignment for rows 34 and 36, per shown in the illustration of FIG. 10.

As the inner tray 28 is formed to hold 13 syringes and the outer tray 2 is formed to hold 12 syringes, a total of 25 syringes may be held in the tray assembly of the instant invention. The numbering on the trays provides an easy correlation of the test serums in the various syringes so that ready identification can be made on which of the test serums causes an allergic reaction in a patient.

Figure 5A:
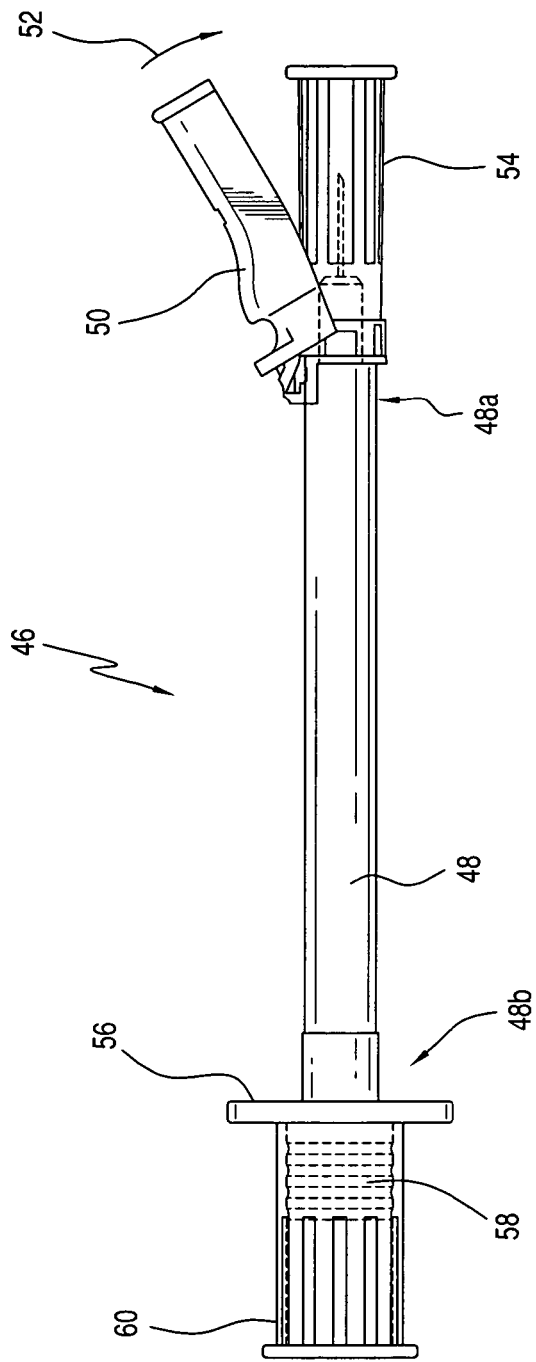
FIG. 5a is a side illustration of one of the syringes that are stored in the FIGS. 1 and 3 trays.

So that inner tray 28 can be fitted into base tray 2, with its top surface 42 in flush relationship with top surface 20 of base tray 2, there is a lip 44 at the outer periphery of insert tray 28 that rests onto the indented shoulder of the base tray 2, when insert tray is placed into base tray 2. To remove insert tray 28 from base tray 24, a user would insert his finger(s) into space 24 provided at base tray 2 to lift up insert tray 28. The longitudinal areas 6a-6c and 32a-32c for base tray 2 and insert tray 28, respectively, are designed such that the body of the syringe is securely held by respective adjacent pairs of posts at the two rows of aligned posts 8 and 10 for base tray 2 and 34 and 36 for insert tray 28. Longitudinal areas 6b and 32b for the trays are designed to have sufficient space to accommodate the needle protective housing of the syringe as shown in FIG. 5a, to be discussed infra. To provide sufficient space, longitudinal area 6b and 32b are configured to slope downwards away from rows 8 and 34, respectively, per shown in FIGS. 2c and 4c per slanting surfaces 4d and 30d. The longitudinal areas 6c for tray 2 and 32c for tray 28 in turn are configured to have sufficient dimension to accommodate the capped plunger end of the syringe. Insert tray 28 may also be molded to have the same color as the base tray 2 for identifying the gauge of the needle of the syringes stored therein.

Figure 5B:
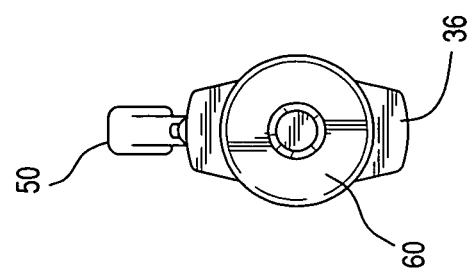
FIG. 5b is an end view of the FIG. 5a syringe, seen from the plunger end of the syringe.
Figure 7A:
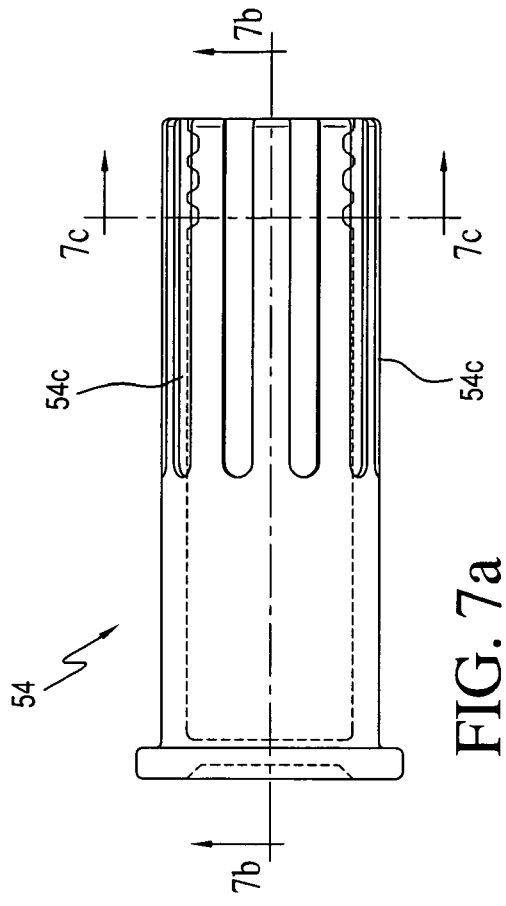
FIG. 7a is a side view of the FIG. 6 sheath.
Figure 7C:
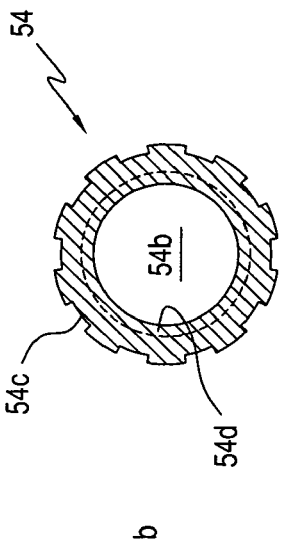
FIG. 7c is a cross-sectional view along section D-D of the FIG. 7a sheath.
Figure 7B:
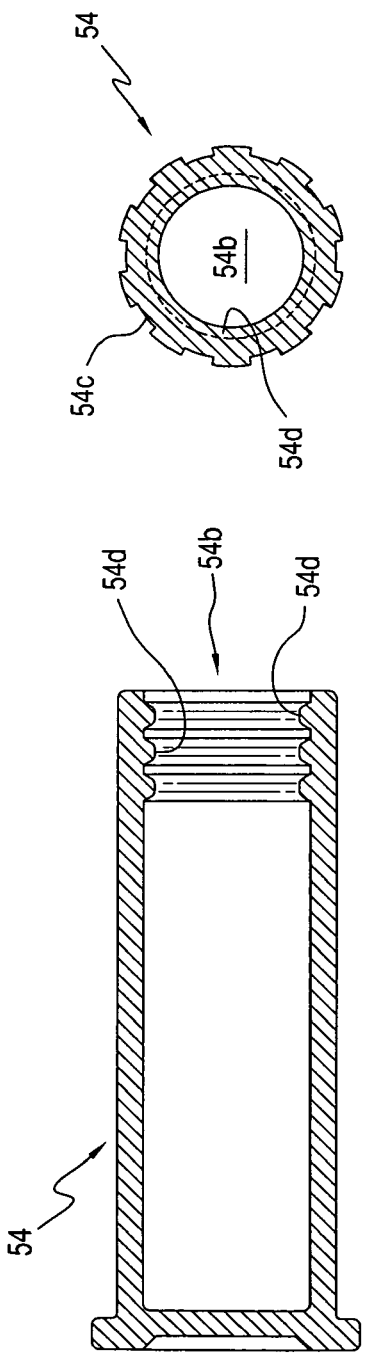
FIG. 7b is a cross-sectional view along section A-A of the FIG. 7a sheath.
Figure 6:
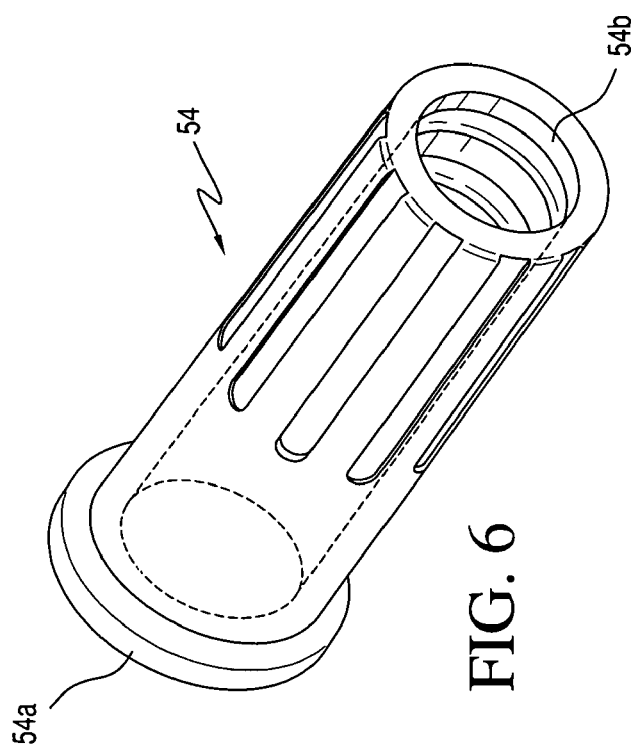

With reference to FIGS. 5a and 5b, an exemplar syringe, for example an allergy testing syringe 46, is shown. Syringe 46 has a body 48 that has a distal or needle end 48a and a proximal or plunger end 48b. There is fitted to the needle end, around the neck thereof, a needle protective housing 50 that is pivotable in the direction indicated by directional arrow 52 for covering a needle (not shown) that, prior to use, is covered by a needle sheath 54. The connection of the housing 50 to the needle end, as well as the covering of the needle prior to use by sheath 54 may be gleaned from U.S. Pat. No. 7,250,038, assigned to the same assignee as the instant invention. The disclosure of the '038 patent is incorporated by reference herein.

At the plunger end 48b of syringe 46 there is a finger flange 56. But unlike most other syringes, there is extending from finger flange 56 an annular extension or well 58 dimensioned to both allow the movement of the plunger rod (not shown for the sake of clarity) and the covering of the plunger and its thumb pad by a cap 60. Sheath 54 is better shown in FIGS. 6 and 7a-7c, while cap 60 is more particularly illustrated in FIG. 8 and FIGS. 9a-9c.

As shown, sheath 54 is a cylindrical covering, with a flat end 54a and an opening 54b that fits onto the luer of the needle end 48a of syringe 46. As best shown in the side view of FIG. 7a, to assist in the handling, a number of grooves 54c are provided on the outer surface of sheath 54. At open end 54b there are a number of circumferential ridges or protuberances 54d that enable sheath 54 to sealingly and tightly fit to the luer of needle 48a. Thus, once covered, the needle extending from the luer at the needle end 48a of syringe 46 is tightly sealed and remains sterile, after the syringe has gone through the sterilization process.

With reference to FIGS. 8 and 9a-9c, cap 60 is shown to have a closed end 60a and an open end 60b. As shown in the perspective view of FIG. 8 and the side view of FIG. 9, a number of grooves 60c are provided circumferentially about the body of cap 60 to assist in the handling of the cap. A number of circumferential ridges 60d are formed at the opening 60d of cap 60 to enable cap 60 to tightly and sealingly fit over annular extension 58 at the plunger end 48b of syringe 46. With cap 60 sealingly and tightly fitted to extension 58 and sheath 54 tightly and sealingly connected to the luer or neck at needle end 48a, the inside of syringe 46 which includes its plunger and the needle extending from its luer are not exposed to the environment, and the fluid path for the syringe is therefore sterile and remains sterile until the sheath 54 and/or the cap 58 is removed from the respective needle end 48a and the plunger end 48b. Given that both end 54a of sheath 54 and end 50a of cap 60 are flat, the syringe may be positioned standing up. As noted before, the longitudinal areas 6a-6c of tray 2 and 32a-32c are dimensioned to accommodate cap 60, sheath 54 and housing 50 inside those trays, as the syringe body 48 is firmly held by the respective adjacent posts in the two rows of posts in the trays.

Figure 10:
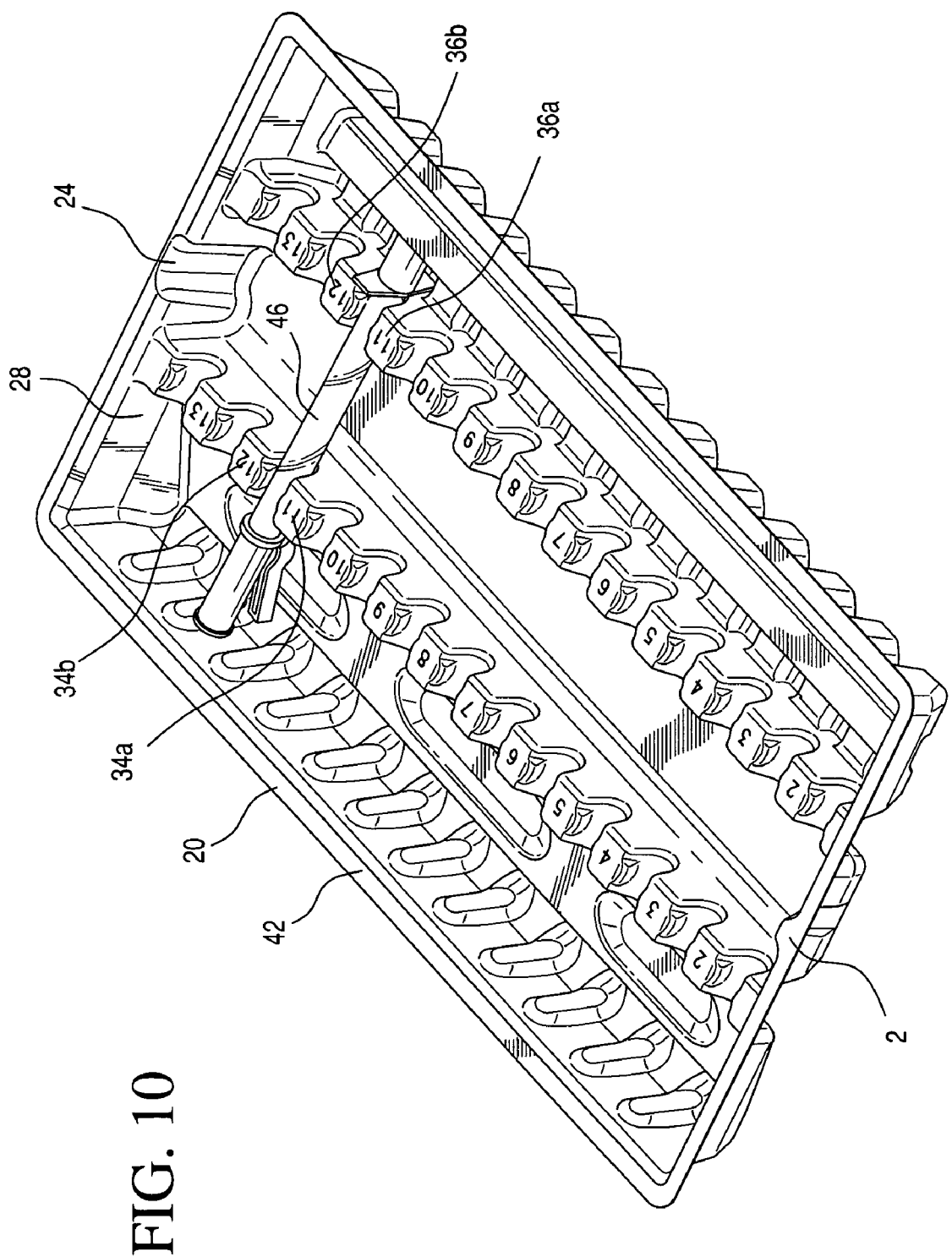
FIG. 10 is an exemplar illustration showing the insert tray fitted to the base tray, and the holding of an allergy testing syringe in a slot of the insert tray.

FIG. 10 is a simplified illustration of the tray assembly of the instant invention in which insert tray 28 has been placed into the base tray 2, with the peripheral lip 44 resting on the indented peripheral shoulder of base tray 2, so that the top surface 42 of insert tray 28 and the top surface of 20 of base tray 2 lie co-planarly. Further shown is an exemplar syringe 46 that has its body removably held by adjacent pairs of posts 34a and 34b and 36a and 36b of the two rows of aligned posts in the insert tray 28. Although one syringe is shown, it should be appreciated that both the insert tray 28 and the base tray 2 may be filled with a plurality of similar allergy testing syringes. The cover sheet is not shown in FIG. 10 for ease of illustration.

Once sealed by the cover sheet, the tray assembly the instant invention is passed through a sterilization process whereby the trays may be exposed to gamma radiation for a period of time. After the sterilization process, the syringes stored in the tray assembly will remain doubly isolated from the environment due to each syringe having both its needle end and plunger end sheathed and capped, respectively, and the trays having been sealed by the cover sheet. That each syringe is individually sterile, even after the cover sheet is removed from the tray, means that the syringes are doubly protected in terms of their isolation from the environment and their sterility prior to use.

Housing 50 and sheath 54 are molded to have a color that corresponds to the gauge of the needle. This color coding may be done by adding respective color pigments to the medical plastics during the molding process and may follow the accepted international standards of colors used for medical devices. Given that both the housing 50 and sheath 54 are color coded to reflect the gauge of the needle covered by sheath 54 prior to use means that a user can look at the protective housing and/or the sheath to determine the gauge of the needle of the syringe, without actually having to look at the needle by removing the sheath. Furthermore, by printing whatever markings on the cover sheet in the same color as the color of the housing and the sheath, a clinician can readily determine the gauge of the needles and the syringes stored in the trays of the tray assembly, without having to remove the cover sheet. As was discussed above, for allergy syringe needles that are for example 27 gauge, the color for the cover sheet markings, as well as the housing and the sheath are all gray.

Alternatively, the cover sheet itself may be gray with the markings in some other color for providing the identification of the gauge of the needles of the syringes stored in the trays. Moreover, with or without color coding the cover sheet, the base tray, and possibly also the insert tray, may be color coded to reflect the needle gauge of the syringes stored in the trays. Thus, a tray assembly containing the exemplar 27 gauge allergy testing syringes is color coded in gray at least at its cover sheet, while a tray assembly that has stored therein syringes of a different gauged needle may be color coded in some other color, for example orange, blue, etc. that represents the gauge of the needle for those syringes.

Inasmuch as the present invention is subject to many variations, modifications and changes in detail, it is intended that all matters described throughout this specification and shown in the accompanying drawings be interpreted as illustrative only and not in a limiting sense. Accordingly, it is intended that the invention be limited only the spirit and scope of the hereto appended claims.

The invention claimed is:

1. A tray assembly comprising: a one piece molded base tray and a one piece molded insert tray, each of the insert and base trays having a plurality of slots each adapted to removably hold a syringe, the base tray having a top with an indented inner periphery configured to hold an outer peripheral lip of the insert tray so that respective top peripheral surfaces of the insert and base trays lie along the same plane when the insert tray is fittingly placed into the base tray, a plurality of syringes each fitted to a corresponding one of the slots, the slots being numbered for assigning a particular number to each of the syringes, each of the syringes having a needle end wherefrom a needle extends and a plunger end wherethrough a plunger is movable, a sheath sealingly covering the needle end and a cap sealingly covering the plunger end of each of the syringes so that each syringe remains sterile prior to use, a cover sheet sealingly and removably bonded to at least the top peripheral surface of the base tray for maintaining sterility inside the insert and base trays and shielding the syringes stored therein from the environment.

2. Assembly of claim 1, wherein each of the syringes has a protective housing at its needle end that pivots to cover the needle after the sheath has been removed from the needle end, the sheath and the housing both are molded to have the same color coded to represent the gauge of the needle.

3. Assembly of claim 2, wherein all the syringes in the trays have the same color coded sheath and needle protective housing, and wherein printings on the cover sheet have the same color as the sheath and the housing.

4. Assembly of claim 1, wherein the syringes are respectively filled with different allergy reactant serums for use with a patient to determine whether the patient is susceptible to different allergic reactions, each numbered slot providing a reference to the allergy reactant serum filled in the syringe held in said each slot.

5. Assembly of claim 1, wherein the plunger end of each of the syringes has a finger flange and an annular well extending from the flange toward the thumb pad of the plunger, the well having a diameter that enables the cap to be sealingly fitted thereto.

6. Assembly of claim 1, wherein each of the trays is molded as a one piece unitary styrene tray.

7. Assembly of claim 1, wherein the cover sheet is made from an air impermeable material.

8. Assembly of claim 1, wherein each of the trays is molded to have three longitudinal areas separated by two rows of aligned posts, adjacent posts at each of the rows separated by a space so that two in alignment corresponding spaces at each of the rows of posts form a slot for a syringe, ridges formed at opposed surfaces of adjacent posts act to frictionally hold the body of the syringe between the adjacent posts when the syringe is placed in a slot.

9. In combination, a one piece molded base tray and a one piece molded insert tray, each of the insert and base trays having a plurality of slots each adapted to removably hold a syringe, the slots being consecutively numbered starting from one of the trays and continuing to other of the trays, the base tray having a top with an indented inner periphery configured to hold an outer peripheral lip of the insert tray so that respective top peripheral surfaces of the insert and base trays lie coplanarly when the insert tray is fittingly placed into the base tray; a plurality of syringes each fitted to a corresponding one of the slots in the trays such that a particular number is assigned to each of the syringes, each of the syringes having a needle end wherefrom a needle extends and whereto a needle protective housing is attached and a plunger end wherethrough a plunger is movable, a sheath sealingly covering the needle end and a cap sealingly covering the plunger end of each of the syringes so that each syringe remains sterile prior to use; and a cover sheet sealingly and removably bonded to at least the top peripheral surface of the base tray for maintaining sterility inside the trays and shielding the syringes stored in the trays from the environment.

10. Combination of claim 9, wherein the protective housing at the needle end of each of the syringes pivots to cover the needle after the sheath has been removed from the needle end, the sheath and the housing both are molded to have the same color coded to represent the gauge of the needle.

11. Combination of claim 9, wherein the needles of all of the syringes in the trays are of the same needle gauge, the sheath and needle protective housing of all of the syringes in the trays are color coded in the same color to correspond to the needle gauge of the needles; and wherein printings on the cover sheet are printed in the same color coded to correspond to the needle gauge of the needles of the syringes in the trays.

12. Combination of claim 9, wherein the syringes are respectively filled with different allergy reactant serums for use with a patient to determine whether the patient is susceptible to different allergic reactions, each numbered slot providing a reference to the allergy reactant serum filled in the syringe held in said each slot.

13. Combination of claim 9, wherein the plunger end of each of the syringes has a finger flange and an annular well extending from the flange toward the thumb pad of the plunger, the well having a diameter that enables the cap to be sealingly fitted thereto.

14. Combination of claim 9, wherein each of the trays is molded to have three longitudinal areas separated by two rows of aligned posts, adjacent posts at each of the rows separated by a space so that two in alignment corresponding spaces at each of the rows of posts form a slot for a syringe, ridges formed at opposed surfaces of adjacent posts act to frictionally hold the body of the syringe between the adjacent posts when the syringe is placed in a slot.

15. A method of providing a tray assembly containing a plurality of syringes for use by a patient, comprising the steps of:
molding a one piece base tray having a top with an indented inner periphery and a plurality of slots each adapted to removably hold a syringe;
molding a one piece insert tray having an outer peripheral lip adapted to rest on the indented inner periphery of the base tray so that respective top peripheral surfaces of the insert and base trays lie coplanarly when the insert tray is placed into the base tray, the insert tray further having a plurality of slots each adapted to removably hold a syringe, wherein the slots in the insert and base trays are consecutively numbered starting from one of the trays and continuing to other of the trays;
storing a plurality of syringes each to a corresponding one of the slots in the insert and base trays such that a particular number is assigned to each of the syringes, each of the syringes having a needle end wherefrom a needle extends and whereto a needle protective housing is attached and a plunger end wherethrough a plunger is movable, a sheath sealingly covering the needle end and a cap sealingly covering the plunger end of each of the syringes so that each syringe remains sterile prior to use;
placing the insert tray into the base tray; and
sealingly bonding a removable cover sheet to at least the top peripheral surface of the base tray for shielding the syringes stored in the trays from the environment.

16. Method of claim 15, wherein the protective housing and the sheath at the needle end of each of the syringes are molded to have the same color coded to represent the gauge of the needle.

17. Method of claim 15, wherein the needles of all of the syringes in the trays are of the same needle gauge, further comprising the steps of:
color coding the sheath and needle protective housing of all of the syringes in the trays in the same color to correspond to the needle gauge of the needles; and
printing information on the cover sheet in the same color as the color coded to correspond to the needle gauge of the needles of the syringes in the trays.

18. Method of claim 15, further comprising the steps of:
filling at least some of the syringes in the trays with different allergy reactant serums for use with a patient to determine whether the patient is susceptible to different allergic reactions; and
determining the different allergy reactant serums in the syringes by referencing each syringe to its numbered slot in the trays.

19. Method of claim 15, further comprising the step of:
forming at the plunger end of each of the syringes a finger flange and an annular well extending from the flange toward the thumb pad of the plunger, the well having a diameter that enables the cap to be sealingly fitted thereto.

20. Method of claim 15, wherein each of the molding steps further comprises the steps of:
molding the tray to have three longitudinal areas separated by two rows of aligned posts;
molding adjacent posts at each of the rows separated by a space to establish a slot for a syringe from two in alignment corresponding spaces at each of the rows of posts; and
molding ridges at opposed surfaces of adjacent posts to frictionally hold the body of the syringe between the adjacent posts when the syringe is placed therebetween.

* * * * *